United States Patent [19]

Hanson

[11] Patent Number: 4,583,944
[45] Date of Patent: Apr. 22, 1986

[54] ORTHODONTIC DEVICES
[75] Inventor: Gustaf H. Hanson, Hamilton, Canada
[73] Assignee: Augusta Developments Inc., Hamilton, Canada
[21] Appl. No.: 690,211
[22] Filed: Jan. 10, 1985
[51] Int. Cl.⁴ ............................................. A61C 7/00
[52] U.S. Cl. .................................................... 433/22
[58] Field of Search .................................. 433/22, 17
[56] References Cited
U.S. PATENT DOCUMENTS
986,076 3/1911 Montag ................................. 433/17
1,938,428 12/1933 Johnson ................................ 433/22

Primary Examiner—Robert Peshock
Attorney, Agent, or Firm—Hirons, Rogers & Scott

[57] ABSTRACT

The invention provides a new orthodontic device for use with the arch wire that is employed in an orthodontic procedure to connect together the orthodontic brackets attached to the teeth. The device comprises a core member having an axial bore to permit it to be threaded onto the wire, the external face of the core member being frustro-conical. The core member is pressed axially into a cylindrical sleeve having a tapered inner face complementary to the core frustro-conical outer face, and the core has a longitudinal slit in its circumference extending from the outer face to the bore so that as it is forced into the sleeve it can clamp tightly onto the wire. The device preferably is used with special pliers having ends which are slotted to fit over the wire and recessed to embrace the device, so that as the pliers ends are closed together the core is forced into the sleeve. The device can be used per se as an end stop, e.g. to stop relative axial movements between the wire and a bracket. A number of different members can be attached to the exterior of the sleeve so as to be fastened by the device to the arch wire, such as an elastic-engaging hook, a tooth-engaging torquing device, a spring device, and a Herbst appliance.

10 Claims, 16 Drawing Figures

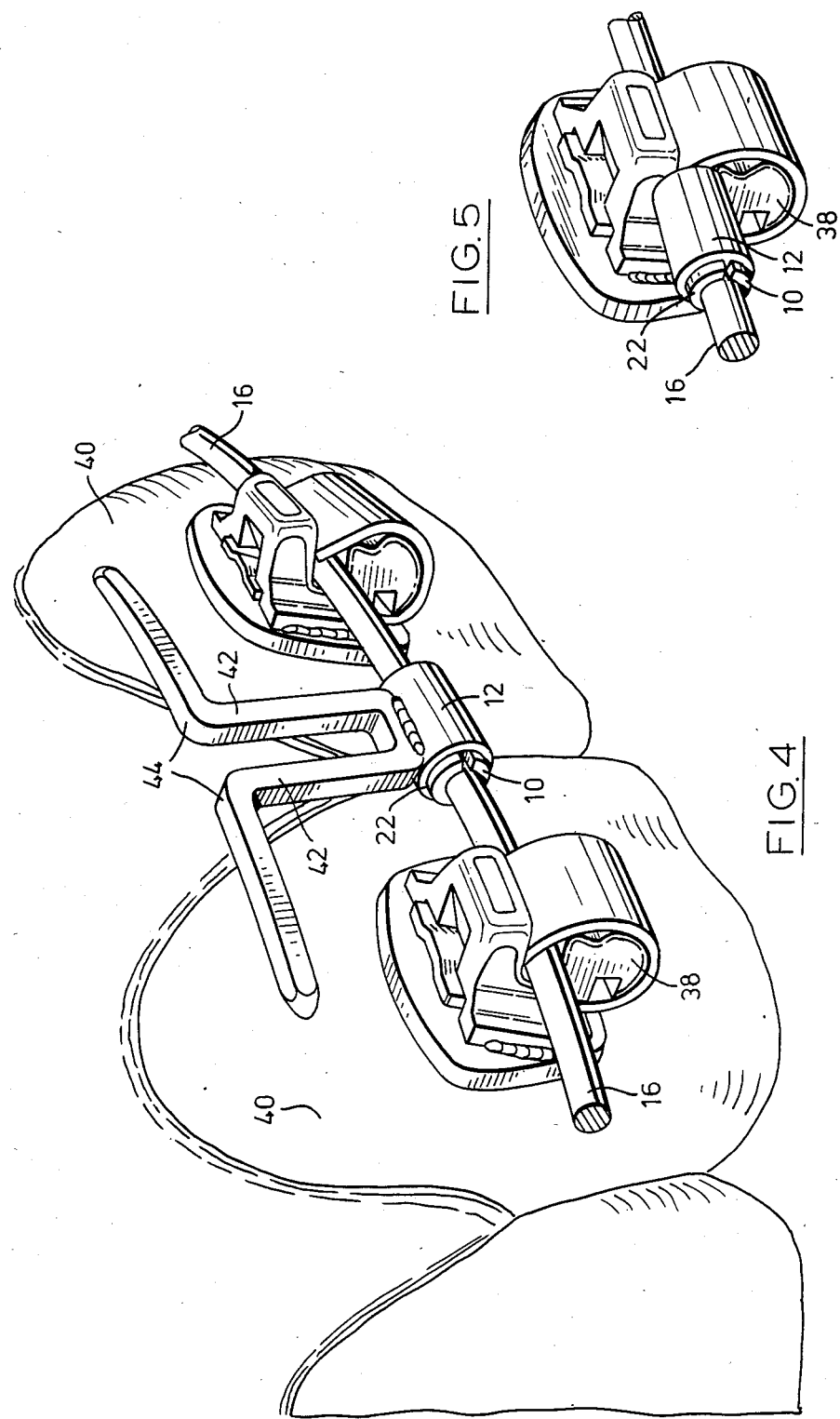

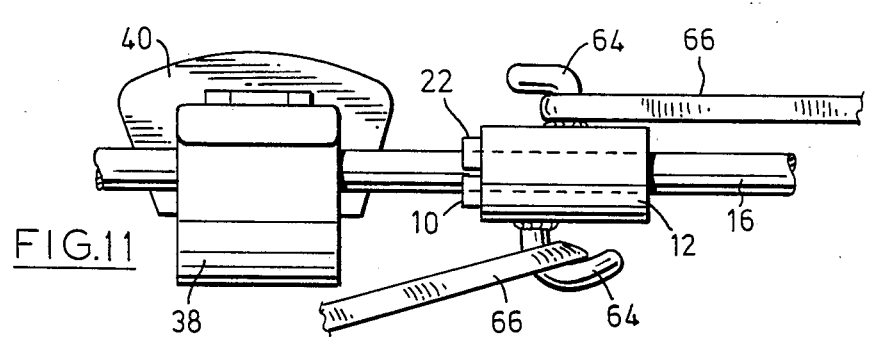
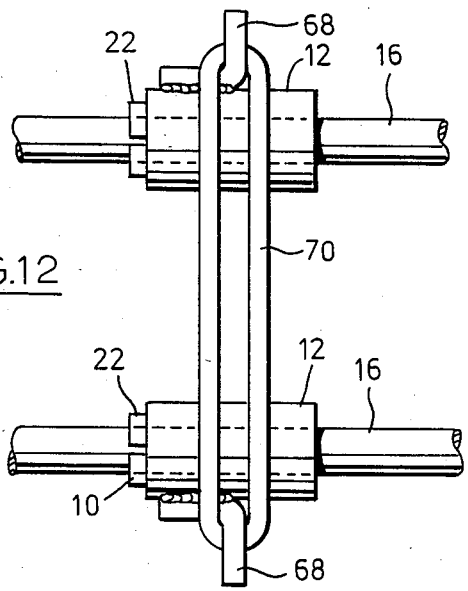
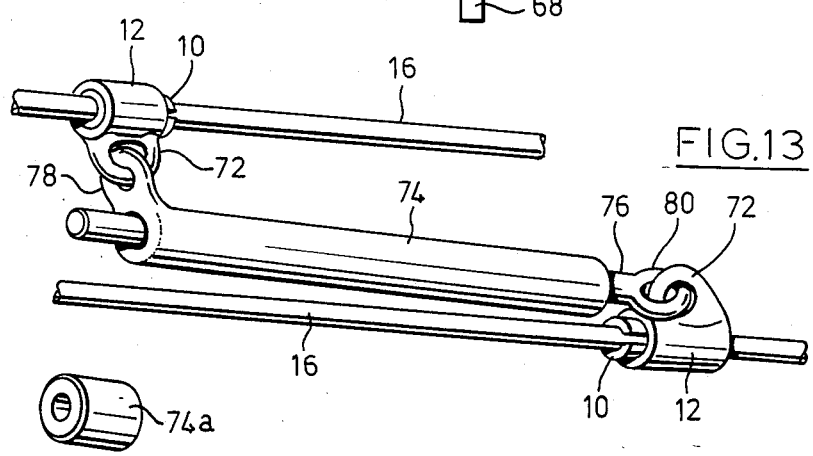

ORTHODONTIC DEVICES

FIELD OF THE INVENTION

The present invention is concerned with improvements in or relating to orthodontic devices for use in conjunction with the arch wires employed in orthodontic procedures.

REVIEW OF THE PRIOR ART

The most common orthodontic procedure now employed is to mount an orthodontic bracket on each of the affected teeth in a row, either by means of a band which encircles the tooth, or increasingly by cementing the brackets directly to the teeth, and then to connect the row of brackets together by means of an arch wire of predetermined stiffness, which applies required corrective forces to the brackets and thus to the teeth. A number of associated orthodontic devices are also used in these procedures, such as anchors for anchoring the ends of the arch wire against axial movement, and latex elastics that are looped under tension between brackets to apply longitudinal forces between them.

DEFINITION OF THE INVENTION

It is an object of the invention to provide a new orthodontic device for use with an orthodontic arch wire.

In accordance with the present invention there is provided a new orthodontic device for attachment to an orthodontic arch wire at a selected location. The device includes a core member having a longitudinal axial bore for reception of an arch wire and so as to permit the core member to be slidably engaged on the arch wire. The core member has a longitudinally-extending frustro-conical exterior face, the core member having a longitudinal slit extending from the exterior face to the axial bore to permit deformation of the core member radially to grip an arch wire disposed within the axial bore. A hollow external sleeve has an interior face complementing said exterior face of the core member and so that with the core member mounted in the sleeve and about the wire, relative axial movement of the sleeve with respect to the core member to insert the core member into the sleeve will deform the core member radially inwards to clamp the device onto the arch wire.

Such a device may be used in combination with pliers having recesses for locating the pliers on opposite ends of the device without interfering with the arch wire, closing of the pliers causing the required relative axial movement.

The device may advantageously have different members attached to the exterior surface of the cylindrical sleeve, such as for example an elastic-engaging hook, a torquing member, or a spring-providing member.

DESCRIPTION OF THE DRAWINGS

Orthodontic devices which are particular preferred embodiments of the invention will now be described, by way of example, with reference to the accompanying diagrammatic drawings, wherein:

FIG. 4 is a perspective view of a device which is a second embodiment, employed for applying torque to teeth and shown applied to an arch wire extending between two brackets, FIGS. 5 is a perspective view of a device which is a third embodiment employed as an end stop for preventing movement of an associated device longitudinally along the wire, FIGS. 8 through 12 show further embodiments of the device for different respective uses in orthodontic procedures, FIG. 13 is a perspective view showing, the use of a device of the invention as an integral component of another orthodontic device known as a Herbst appliance, FIG. 13a is a perspective view of a spacing sleeve portion employed with the device of FIG. 12.

DESCRIPTION OF THE PREFERRED EMBODIMENTS

Figure 1:
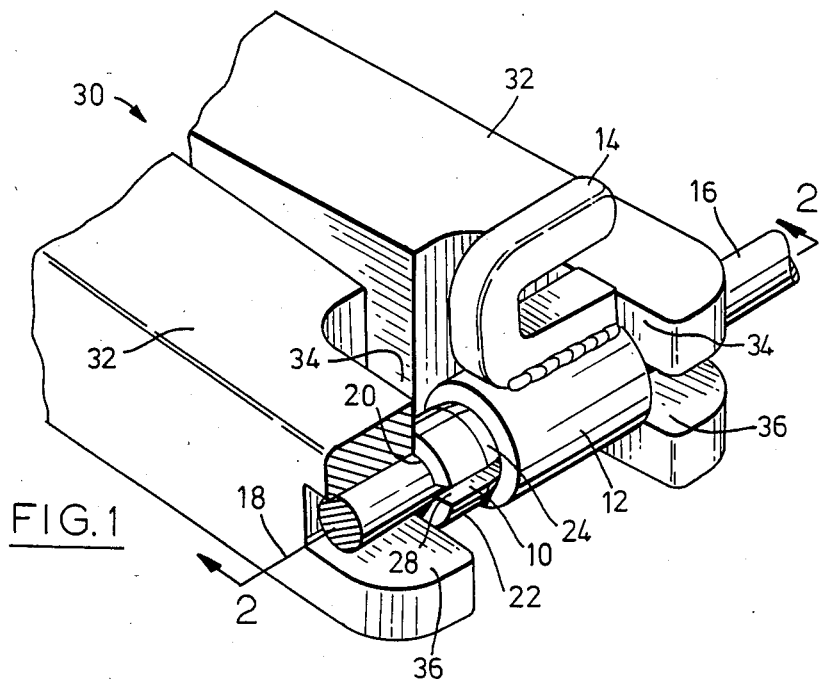
FIG. 1 is a perspective view of a device which is a first embodiment shown mounted on a cylindrical arch wire ready for clamping thereon, and a corresponding view of the operative ends of a pair of pliers employed for that purpose.
Figure 2:
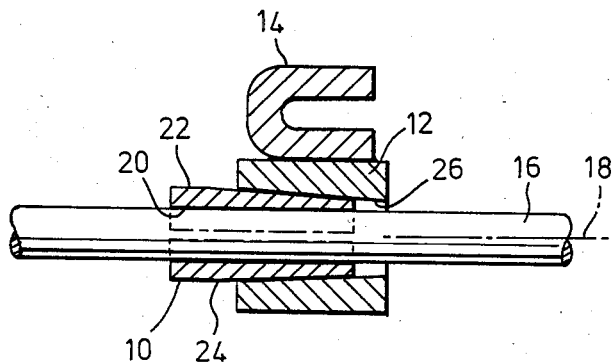
FIG. 2 is a cross-section through the device of FIG. 1, taken on the line 2—2 of FIG. 1.

Reference is now made to FIGS. 1 and 2, which illustrate a first embodiment consisting of a core member 10 and a hollow external sleeve 12 having with this embodiment an occlusially-extending elastic-retaining hook 14 fixed thereto, as by welding. This particular embodiment is intended to be used with an arch wire 16 of circular transverse cross-section having a longitudinal axis 18. As seen in FIG. 2, the core member has a longitudinal bore 20 of transverse cross-section corresponding to that of the wire 16 and so that the core member is a close sliding fit over the wire for placement in the desired position. The external cylindrical face of the core member has a short uniform diameter cylindrical portion 22 and a frustro-conical portion 24 which reduces in diameter from the portion 22 toward the other end. In this embodiment the angle between the axis and the taper generator is about 3.5 degrees. The inside cylindrical face 26 (FIG. 2) of the sleeve 12 is also tapered with about the same taper angle from one end to the other, so that the two faces 24 and 26 are complementary. In operation the smaller diameter end of the core is inserted into the larger internal diameter end of the sleeve and pushed home by hand to about the relative positions illustrated by FIG. 1. The core member is provided with a longitudinal slot or slit 28 that extends radially from the bore 20 to its exterior surface, the slit being of sufficient circumferential extent to permit the core member to be compressed radially inwards to clamp the device securely onto the wire against both rotational and longitudinal movements upon relative axial movement forcing the core further into the sleeve. The hook 14 is now available to act as a retainer for an elastic used in the orthodontic procedure.

Figure 3:
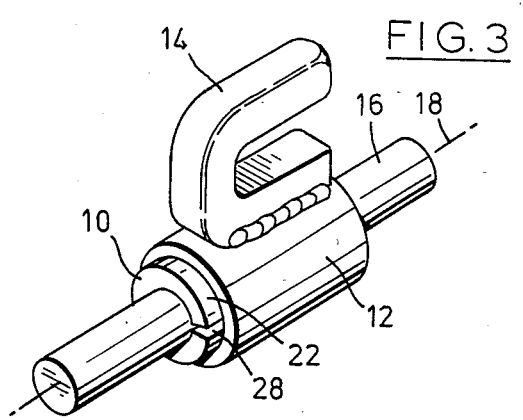
FIG. 3 is a perspective view similar to FIG. 1 showing the device clamped onto the wire.

The core member and sleeve may conveniently be moved axially relative to one another by use of a special pair of pliers 30 (FIG. 1 only) comprising two closable legs 32 provided at their ends with two opposed recesses 34 that will receive the device in unclamped condition. The leg ends are also provided with respective aligned slots 36 just large enough to receive the arch wire, so that the adjacent edge portions of their opposed faces around the slots 36 will engage respectively one radial face of the sleeve 12 and the opposite radial face of the core member 10. Closing the plier legs by hand in the usual manner will drive the core longitudinally of the axis 18 into the sleeve with the force necessary to clamp the device firmly to the arch wire. This clamped configuration is illustrated by FIG. 3.

In a particular preferred embodiment the cylindrical sleeve 12 is of 304 stainless steel, has an external diameter of 1.15 mm (0.045 inch) and is 1.5 mm (0.060 inch) in length; the internal bore is of circular transverse cross-section and tapers from a diameter of 0.81 mm (0.032 inch) to 0.58 mm (0.023 inch). The core 10 is of the same material and of overall length 1.65 mm (0.065 inch) while the tapered portion is of 1.4 mm (0.055 inch) length; the maximum external diameter is 0.81 mm (0.032 inch) and it tapers downward to a minimum external diameter of 0.63 mm (0.25 inch). The bore is of 0.48mm (0.019 inch) diameter and the slot is of 0.13 mm (0.005 inch) circumferential width. The values given are of course the average values and take no account of manufacturing tolerances which are relatively significant in a device of such small size, but will be apparent to those skilled in the manufacture of very small parts.

FIG. 4 shows a second device embodying the invention employed as a "torquing auxiliary", the device in operation being mounted on an arch wire 16 that extends between two orthodontic brackets 38 cemented to respective upper central incisors 40. The brackets 38 are for example as disclosed and claimed in my U.S. Pat. Nos. 3,772,787; 4,248,588 and 4,492,573 issued respectively June 7, 1983, Feb. 3, 1981 and Jan. 8, 1985, the disclosures of which are embodied herein by this reference. The device comprises an essentially T-shaped member comprising occlusially extending foot portions 42 attached to the sleeve 12 and mesially-distally extending arm portions 44. The device is clamped to the arch wire with the arm portions pressing firmly against the teeth adjacent their roots in a manner to move them palatally. A similar device for use only with a single tooth will have only a single foot portion 42 and arm portion 44.

FIG. 5 of the drawings shows the basic device of the invention mounted on arch wire 16 and butted against a side wall of a bracket 38 so as to function to anchor the arch wire against axial movement in the corresponding direction; it can therefore also be used as an end-anchor for the wire. A second stop member of the invention can be used on the other side of the bracket if constraint is required in both directions.

Figure 6:
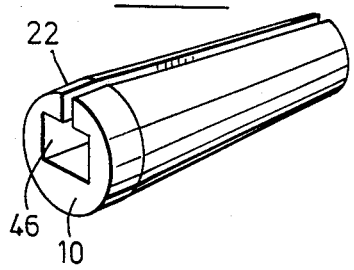
FIGS. 6 and 7 are perspective views of core members for use respectively with rectangular cross-section wires and Hanson "SPEED" (Trade Mark) wires.
Figure 7:
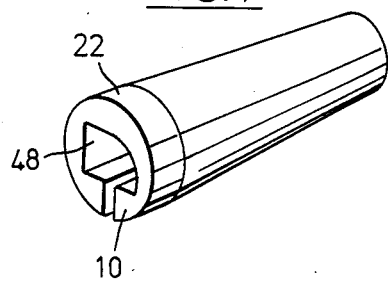

FIG. 6 shows the configuration of a core member 10 with a bore 46 intended to receive an arch wire 16 of rectangular transverse cross-section, rather than the round cross-section so far illustrated, while FIG. 7 shows the configuration for an arch wire of the special transverse cross-section disclosed ad claimed in my U.S. Pat. No. 4,386,909, issued June 7, 1983, the disclosure of which is incorporated herein by this reference, the bore 48 being of this special cross-section. It will be appreciated that wires with these special cross-sections can also be used with a core member having a cylindrical bore provided that the material used for the core member will deform to the necessary extent upon being squeezed into the sleeve.

Figure 8:
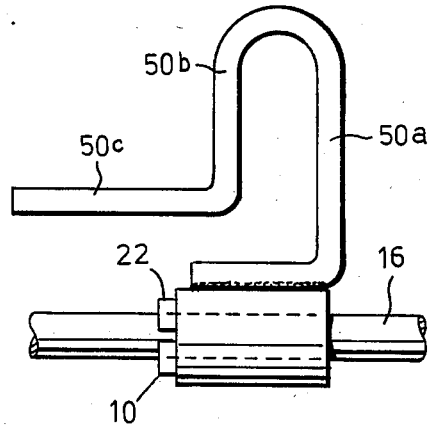

FIG. 8 illustrates another "torquing auxiliary" embodiment in which the attachment to the sleeve 12 has an occlusially-extending portion 50a and a shorter gingivally-extending portion 50b, with the latter terminating in a mesially-distally-extending arm portion 50c; the device can therefore be used to provide torquing forces to the teeth much closer to the arch wire than is possible with the device of FIG. 4.

Figure 9:
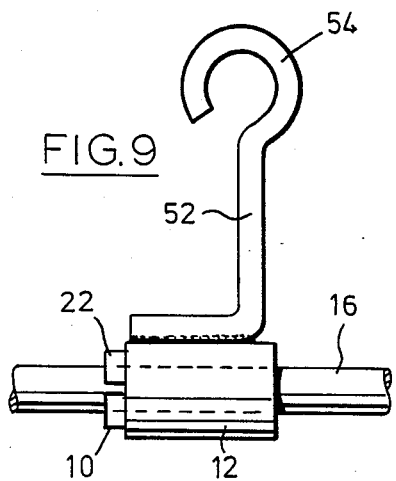
Figure 10:
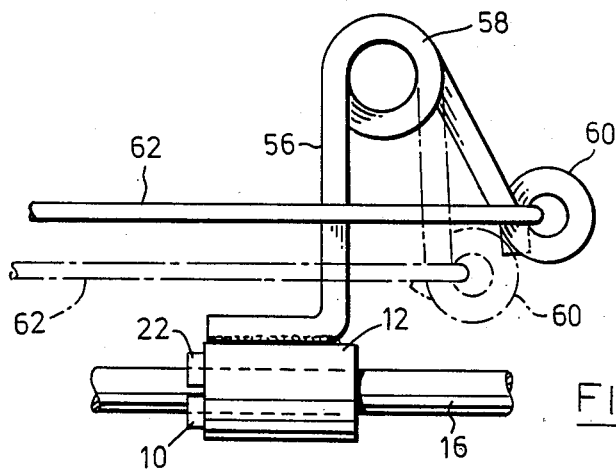

FIG. 9 ilustrates a device with a relatively long gingivally-extending arm member 52 terminating in an elastic-engaging hook 54, while FIG. 10 illustrates an embodiment which permits the latex elastics commonly used in orthodontic procedures to be replaced by a more permanent wire and spring connector. Thus a gingivally-extending arm member 56 of spring material includes a helical spring-providing loop 58 that will give mesial-distal extending tension over a relatively long range of activation and without having to bend the arch wire. The arm member terminates in a wire-engaging loop 60 that has wire 62 attached thereto. This type of retraction device has an advantage over conventional retraction or closing loops employed hitherto by bending the arch wire, in that the wire 62 remains parallel to the arch wire 16 as the spring extends, e.g. from the position shown in broken lines to that shown in solid lines, avoiding changes in its inclination that render the procedure more difficult to apply.

FIG. 11 illustrates an embodiment in which two diametrically-opposed small hooks 64 are provided and employed as anchors for elastomer loops 66, one hook extending gingivally and the other occlusially, the two facing in opposite directions. FIG. 12 illustrates an embodiment in which each sleeve 12 is provided with a single hook 68 extending gingivally therefrom and also serving as a respective anchor point for a common elastic 70 applying opposite rotational forces to the two parallel arch wires 16.

The devices of the invention can be used as an integral part of what is known as the Herbst appliance, which is designed to hold a patient's lower jaw in a protruded relationship relative to the upper jaw. This appliance can be used to stimulate more rapid forward growth of the lower jaw in children and adolescents. The patient has freedom to move the mandible in any direction except back to its usual retruded position, i.e. the position the lower jaw usually occupies during centric closure. In other words, the patient can open his/her mouth, move the lower jaw left or right or even further forward but never back more than the amount determined by the appliance.

FIG. 13 shows one such appliance comprising two devices mounted on respective arch wires 16. Each sleeve 12 is provided with a respective loop 72 permitting its connection to either sleeve 74 or rod 76 of the appliance, by means of respective loops 78 and 80.

The rod 76 slides freely axially within the sleeve 74 and the distance between the two devices can increase by movement of the rod partly out of the sleeve; it is impossible for the patient to protrude his/his mandible a sufficient amount to disengage the rod from the tube. Opposite movement of the rod into the sleeve is however constrained when the rod is already fully within the sleeve. The two pairs of interengaging loops of the device of FIG. 13 permit the necessary degrees of freedom of movement. The effective length of the sleeve 74 is adjusted by use of small sleeve portions 74a, as illustrated by way of example in FIG. 13a, which are placed on the rod 76 and interposed between the sleeve 74 and the loop 80.

Figure 14:
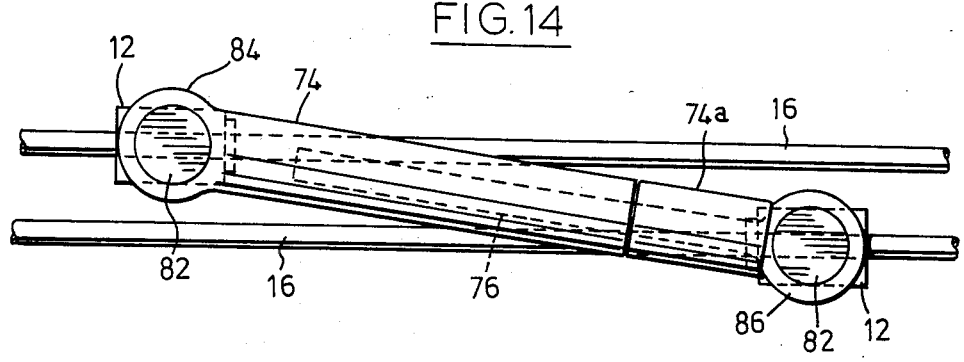
FIG. 14 is a perspective view of a modified form of Herbst appliance that is possible by use of the device of the invention.
Figure 15:
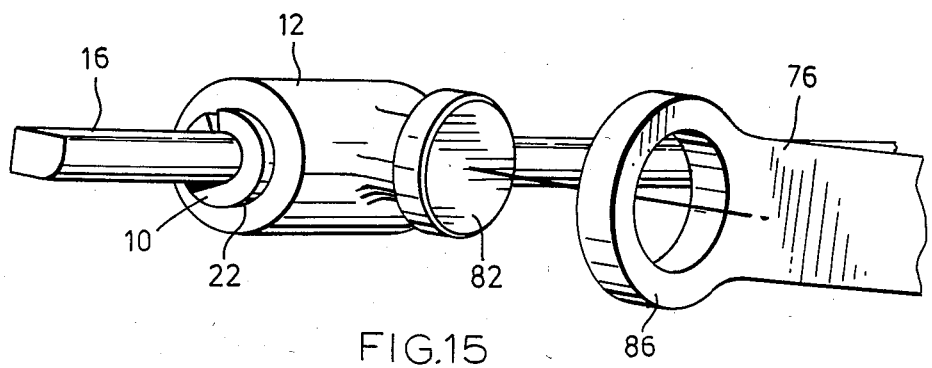
FIG. 15 is a perspective view to an enlarged scale of part of the device of FIG. 14 to show the construction thereof.

In another embodiment illustrated by FIGS. 14 and 15 each sleeve 12 is provided with a headed stud 82, while the sleeve 74 and the rod 76 are provided with respective cylindrical loops 84 and 86, these loops fitting loosely around the shanks of the studs 82 to provide the same degrees of freedom as with the device of FIG. 13. It will be understood that instead the headed studs can be provided on the sleeve and telescoping rod, while the cooperating loops that embrace the stud shanks are provided on the device sleeves 12.

The invention can be modified within the scope of the disclosure and claims.

I claim:

1. In combination, an orthodontic device for attachment to an orthodontic arch wire at a selected location thereon, and a pliers for manipulating the orthodontic device to attach it to the arch wire, the pliers comprising opposed closable legs for engagement with the orthodontic device, and registered slots in the respective leg for receipt of the arch wire, the orthodontic device comprising:
   a core member having a longitudinal axial bore for reception of the arch wire and permitting the core member to be slidably engaged on the arch wire;
   the core member having one end of smaller diameter and the other end of larger diameter with a longitudinally-extending frustro-conical exterior face between the said ends, and a longitudinal slit extending along its length from the exterior face to the axial bore to permit deformation of the core member radially to grip the arch wire disposed within the axial bore; and
   a hollow external sleeve having a tapered interior face with one end of larger internal diameter and the other end of smaller internal diameter complementing said frustro-conical exterior face of the core member and so that with the sleeve mounted about the core member with the core member end of larger diameter protruding from the end of the sleeve of larger internal diameter, and with the opposed plier legs engaged respectively with the larger diameter end of the core member and the smaller internal diameter end of the sleeve, closing of the closable plier legs together produces relative axial movement of the sleeve and the core member to insert the core member into the sleeve and deform the core member radially inwards to clamp the device onto the arch wire at the selected location.

2. A combination as claimed in claim 1, and including a occlusially-extending elastic engaging hook member attached to the outer surface of the sleeve.

3. A combination as claimed in claim 1, and including a occlusially-extending tooth engaging torquing member attached to the outer surface of the cylindrical sleeve; the torquing member comprising an occlusially-extending first portion, connected to a gingivally-extending second portion, which is in turn connected to a mesially-distally extending arm portion for engagement with the teeth.

4. A combination as claimed in claim 1, and including an occlusially-extending tooth engaging torquing member attached to the outer surface of the cylindrical sleeve; the torquing member comprising an occlusially-extending first portion connected to a gingivally-extending second portion, which is in turn connected to a mesially-distally extending arm portion for engagement with the teeth.

5. A combination as claimed in claim 1, and including a spring member attached to the outer surface of the cylindrical sleeve, the spring member comprising an occlusially-extending foot portion connected to a helically-wound spring-providing portion, which is in turn connected to a hooked portion to be sprung thereby for mesial-distal spring action.

6. A combination as claimed in claim 1, and including a labially-extending hook member attached to the outer surface of the cylindrical sleeve.

7. A combination as claimed in claim 1 and including a pair of occlusially-extending hook members attched to the outer surface of the cylindrical sleeve at diametrically opposed locations thereon.

8. A combination as claimed in claim 1, and comprising two such devices, a sleeve member connected to one device and a rod member connected to the other device, the rod sliding within the sleeve to constitute a Herbst appliance.

9. A combination as claimed in claim 8, wherein the connection between each device and the respective sleeve member or rod member are constituted by respective interengaging loops one on the device sleeve and the other on the respective sleeve or rod member.

10. A combination as claimed in claim 8, wherein the connection between each device and the respective sleeve member or rod member is a respective headed stud on one of the device sleeve and the respective sleeve member or rod member, and a loop on the other of the device sleeve and the respective sleeve member or rod member embracing the shank of the respective headed stud.

* * * * *